United States Patent [19]

Sommer et al.

[11] 4,098,814

[45] Jul. 4, 1978

[54] N-PHOSPHONO METHYLENE AMINO ALKANE PHOSPHONIC ACID COMPOUNDS, PROCESS OF PRODUCING SAME, AND METHOD AND COMPOSITIONS OF USING SAME

[75] Inventors: Klaus Sommer, Heidelberg; Guenter Raab, Laudenbach, both of Fed. Rep. of Germany

[73] Assignee: Benckiser-Knapsack GmbH, Ladenburg, Neckar, Fed. Rep. of Germany

[21] Appl. No.: 799,498

[22] Filed: May 23, 1977

[30] Foreign Application Priority Data

Jun. 9, 1976 [DE] Fed. Rep. of Germany ....... 2625727

[51] Int. Cl.$^2$ .......................... C07F 9/38; C02B 5/06; C14C 3/00; D06M 1/14
[52] U.S. Cl. .................................... 260/502.5; 71/27; 162/158; 210/58; 252/8.57; 252/8.8; 252/180
[58] Field of Search ...................................... 260/502.5

[56] References Cited

U.S. PATENT DOCUMENTS

| | | | |
|---|---|---|---|
| 2,599,807 | 6/1952 | Bersworth | 260/502.5 |
| 3,288,846 | 11/1966 | Irani et al. | 260/502.5 |
| 3,705,191 | 12/1972 | Kerst | 260/502.5 |

*Primary Examiner*—Joseph E. Evans
*Attorney, Agent, or Firm*—Bacon & Thomas

[57] ABSTRACT

Valuable and highly water soluble N-phosphono methylene mono- and di-amino alkane mono- and polyphosphonic acids which have not only an >N—CH$_2$—PO$_3$H$_2$ group but also a >C—PO$_3$H$_2$ group in their molecule are produced by reacting amino alkane mono- or diphosphonic acids with formaldehyde and phosphorous acid or alkane nitriles with phosphorous acid, formaldehyde, and concentrated hydrochloric acid. The resulting phosphonic acid compounds are valuable sequestering agents forming complex compounds with bi- and polyvalent metal ions. They are useful for water softening even in substoichiometric amounts, in textile treatment baths, in the paper manufacture, in tanning baths, for the manufacture of liquid fertilizers, and for other purposes.

24 Claims, No Drawings

N-PHOSPHONO METHYLENE AMINO ALKANE PHOSPHONIC ACID COMPOUNDS, PROCESS OF PRODUCING SAME, AND METHOD AND COMPOSITIONS OF USING SAME

BACKGROUND OF THE INVENTION (1) Field of the Invention

The present invention relates to novel and valuable phosphonic acid compounds and more particularly to N-phosphono methylene mono-amino alkane mono- and polyphosphonic acids and to N-phosphono methylene diamino alkane polyphosphonic acids, to a simple and effective process of making such compounds, to methods of using same, and to compositions containing same.

(2) Description of the Prior Art

It is known to react amino carboxylic acids with aldehydes or ketones and compounds of trivalent phosphorus, such as phosphorus trichloride or phosphorous acid. Thus, for instance, according to British Pat. No. 1,142,294 or according to German Published Application No. 12 14 229, there is obtained the corresponding phosphono carboxylic acid by reacting glycine with formaldehyde and phosphorus trichloride in the presence of water or phosphorous acid.

SUMMARY OF THE INVENTION

It is one object of the present invention to provide novel and advantageous N-phosphono methylene mono-amino alkane mono- and polyphosphonic acids or N-phosphono methylene di-amino alkane polyphosphonic acids which have proved to be highly valuable compounds.

Another object of the present invention is to provide a simple and effective process of making such novel phosphonic acid compounds.

Still another object of the present invention is to provide compositions containing such novel amino alkane phosphonic acid compounds, such compositions being useful for various technical applications.

Other objects of the present invention and advantageous features thereof will become apparent as the description proceeds.

In principle, the novel N-phosphono methylene amino alkane phosphonic acid compounds according to the present invention correspond to the following formula

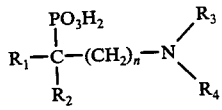

In said formula
$n$ is a numeral from 0 to 4;
$R_1$ represents hydrogen,
  alkyl with 1 to 11 carbon atoms in its hydrocarbon chain,
  hydroxyl,
  an alkylene phosphonic acid group of the formula $-(CH_2)_n\cdot PO_3H_2$,
  the hydroxy ethylene group of the formula $-C_2H_4OH$,
  an alkylene carboxylic acid group of the formula $-(CH_2)_n\cdot COOH$,
  an amino alkylene group of the formula

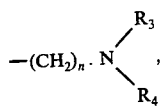

and
an 1-amino alkane-1,1-diphosphonic acid group of the formula

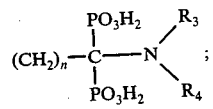

$R_2$ indicates hydrogen or the phosphonic acid group;
$R_3$ indicates hydrogen or the methylene phosphonic acid group; and
$R_4$ indicates the methylene phosphonic acid group.

The novel phosphonic acid compounds according to the present invention differ from the heretofore known compounds more particularly by the feature that they contain, in addition to the group $>N-CH_2-PO_3H_2$ also the group $>C-PO_3H_2$.

Compounds of this type are, for instance, the N-phosphono methylene-1-amino alkane phosphonic acids which may contain up to 11 carbon atoms in their alkane chain.

Other compounds which are comprised by the above-given general formula are the N-phosphono methylene-1-aminoalkane-1,1-diphosphonic acids which may also have up to 11 carbon atoms in their alkane chain.

A further group of compounds according to the present invention are the N-phosphono methylene-1-amino-3-phosphono alkane phosphonic acids.

Futhermore, N-phosphono methylene-1-amino-3-hydroxy alkane diphosphonic acids as well as the N-phosphono methylene-1-amino-ω-carboxy-1,1-alkane diphosphonic acids and the N,N-bis-phosphono methylene diamino alkane tetraphosphonic acids are also to be mentioned.

Amino alkane phosphonic acids are used as starting materials in order to produce the compounds according to the present invention. Said starting materials are subjected to a phosphono alkylation with carbonyl compounds and phosphorous acid or phosphorous trichloride in the presence of water. Preferably aliphatic aldehydes, especially formaldehyde, and ketones are used as carbonyl compounds.

The novel phosphonic acids of the present invention thus can be produced according to the following two processes.

Process A

Amino alkane mono- or, respectively, polyphosphonic acids of the formula

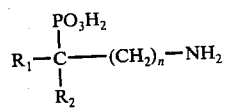

in which
$n$ is a numeral from 0 to 4;
$R_1$ is hydrogen,
  alkyl with 1 to 11 carbon atoms in its hydrocarbon chain, hydroxyl,
a hydroxy ethylene group of the formula $-C_2H_4OH$,
an alkylene phosphonic acid group of the formula $-(CH_2)_n \cdot PO_3H_2$,
an alkylene carboxylic acid group of the formula $-(CH_2)_n-COOH$,
an amino alkylene group of the formula

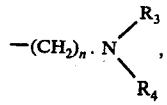

or
an amino alkane-1,1-diphosphonic acid group of the formula

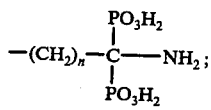

$R_2$ is hydrogen or the phosphonic acid group; and $R_3$ and $R_4$ are hydrogen,
are used as starting materials.

Said starting phosphonic acids are reacted with formaldehyde and phosphorous acid in a proportion of at least 1:1:1.5 to 1:2:2.5. The temperature at which the reaction is carried out is within the range of between 50° C. and about 120° C.

2-Amino ethane-1-phosphonic acid, for instance, yields, on reaction with the corresponding amounts of formaldehyde solution and phosphorous acid, the N,N-bis-phosphono methylene-1-amino ethane monophosphonic acid.

3-Amino propane-1-phosphonic acid yields N-phosphono methylene-3-amino propane-1-phosphonic acid on reaction with formaldehyde and phosphorous acid.

Preferably the reaction is carried out with a small excess of formaldehyde, because using smaller amounts of aldehyde and phosphorous acid than corresponding to the above stated proportions yields mixtures of di- and triphosphonic acids which can be separated only with difficulty.

Of considerable technical importance is the reaction of geminate amino alkane di-phosphonic acids. They yield predominantly triphosphonic acids and, in addition thereto, small amounts of polyphosphonic acids.

Reaction of amino methane diphosphonic acid with slightly more than one mole of phosphorous acid and formaldehyde yields mainly N-phosphono methylene amino methane diphosphonic acid. The reaction proceeds in a similar manner with other 1-amino alkane-1,1-diphosphonic acids such as, for instance, with 1-amino ethane-1,1-diphosphonic acid or with 1-amino propane-1,1-diphosphonic acid.

Hydroxy amino alkane diphosphonic acids yield hydroxy amino alkane triphosphonic acids. 1,2-Diamino ethane-1,1-diphosphonic acid is converted according to the present invention into a mixture of various polyphosphonic acids.

In place of phosphorous acid, there can also be used phosphorus trichloride with the amount of water required to convert it to phosphorous acid.

Process B

Phosphono alkylation for the production of amino alkane diphosphonic acids according to the present invention can be effected especially advantageously by reacting alkane nitriles and phosphorous acid in the molar proportion of 1:2.5 to 1:3 at a temperature between about 140° C. and about 200° C. until a crystalline slurry, which can still be stirred, has been formed. Formaldehyde solution and preferably concentrated hydrochloric acid are added in the required amounts to the resulting mixture cooled to about 120° C. and the mixture is subsequently boiled under reflux. Nitriles which contain 1 to 12 carbon atoms are useful reactants for this process. Aliphatic straight chain or branched alkane nitriles have proved to be useful. Especially preferred nitriles are acetonitrile, propionitrile, butyronitrile, lauronitrile, as well as di-alkoxy phosphono propionitrile.

The new phosphonic acids are distinguished over the prior art phosphonic acids by being readily produced in a good yield and by being highly soluble in water. High water solubility is an important requirement for most uses of the compounds. They are excellent sequestering agents which form complex compounds with bivalent and polyvalent metal ions and thus can be employed with advantage in all those instances where a satisfactory sequestering power is required. Of special importance is their resistance to hydrolysis even at a high temperature. As a result thereof they can be employed in all those cases in which temperatures above 100° C. are required. Thus they can be added to all media in which compounds causing hardness of the water have a disturbing and obnoxious effect or in which the influence of polyvalent metal ions is to be eliminated. More particularly, they have proved to be of considerable value in the processing of hard water, as additives to baths used for the treatment of textiles, in the manufacture of paper, and in tanning baths.

The new phosphonic acid have also proved to be of value in stabilizing the water hardness when added in substoichiometric amounts, i.e. for carrying out the so-called "threshold process".

A further possibility of using the new phosphonic acids consists in their employment for the production of liquid fertilizers. More particularly, the extremely high solubility of the free acids in aqueous media which is lacking in most of the presently known amino phosphonic acids may be especially pointed out. In general, at least 100 g. of the compounds described in the examples and claimed hereinafter, are soluble in 100 ml. of water.

DESCRIPTION OF THE PREFERRED EMBODIMENTS

The following examples serve to illustrate the present invention without, however, limiting the same thereto.

EXAMPLE 1

95 g. of amino methane diphosphonic acid, 50 g. of phosphorous acid, and 60 g. of a 37% formaldehyde solution are heated under reflux with 25 cc. of concentrated hydrochloric acid for two hours. As soon as a clear solution is obtained, the water is removed completely by evaporation and the residue is poured into 300 cc. of methanol. In this manner, non-reacted phosphorous acid is removed.

The resulting resinous residue contains mainly the N-phosphono methylene amino methane diphosphonic acid.

EXAMPLE 2

103 g. of 1-amino ethane-1,1-diphosphonic acid are suspended in 100 g. of a 30% formaldehyde solution. 85 cc. of phosphorus trichloride are added thereto drop by drop while stirring. After the addition is completed, the mixture is heated to boiling until a homogeneous mixture is formed. The water is removed by evaporation in a vacuum. The resulting phosphonic acid mixture is precipitated by the addition of acetone. N-phosphono methylene-1-amino ethane-1,1-diphosphonic acid is obtained in this manner.

EXAMPLE 3

62.5 g. of 2-amino ethane-1-phosphonic acid, 85 g. of phosphorous acid, and 30 g. of trioxane are suspended in 100 cc. of water. 20 cc. of concentrated hydrochloric acid are added thereto. The reaction mixture is boiled under reflux for 3 hours. The water is then removed by evaporation. The resulting mixture is repeatedly washed with acetone or butanone in order to remove excess formaldehyde and phosphorous acid. A product which consists mainly of N,N-bis-phosphono methylene-2-amino ethane-1-phosphonic acid is obtained as residue.

EXAMPLE 4

3,140 g. of phosphorous acid are dissolved in 628 g. of acetonitrile at 80° C. and 1 g. of aluminum chloride is added thereto. Said reaction mixture is added drop by drop, while stirring vigorously, through a dropping funnel which can be heated, into a reaction vessel which is provided with reflux cooler and is heated to 190° C. Crystallization sets in after about half an hour. The speed at which the reaction mixture is added drop by drop is regulated so that the temperature of the mixture in the reaction vessel is maintained between 170° C. and 180° C. Addition of the reactants is complete after three hours. A homogeneous crystalline slurry which can still be stirred, is obtained. The reaction mixture is then cooled to 120° C. 3.26 liters of concentrated hydrochloric acid and 2.8 liters of a 36% formaldehyde solution are added thereto and the mixture is boiled under reflux for three hours.

An amber colored solution which still contains some solid matter is obtained. After addition of 400 g. of phosphorous acid and boiling the mixture under reflux for one hour, a clear amber colored solution is produced. By thin-layer chromatographic investigation it could be shown that the 1-amino ethane-1,1-diphosphonic acid was completely converted into two novel phosphonic acids and that only a small amount of phosphorous acid and only traces of phosphoric acid are present in the solution. One of the resulting phosphonic acids which is obtained predominantly has been isolated and identified by its $^{31}$P-resonance spectrum as well as by its infrared spectrum and also by analysis as N-phosphono methylene-1-amino ethane-1,1-diphosphonic acid.

Analysis: Calculated: C,12.04%; N,4.68%; P,31.10%; Found: C,12.3%; N,4.9%; P,31.3%.

When using the following amino alkane phosphonic acids or alkane nitriles as the one reaction component and otherwise proceeding as described in the aforesaid examples, the following compounds are obtained:

| Example | Alkane reactant | Resulting amino alkane phosphonic acid | Prepared according to Example |
|---|---|---|---|
| 5 | 1-Amino propane-1,1-diphosphonic acid | N-phosphono methylene-1-amino propane-1,1-diphosphonic acid | 1 |
| 6 | 1-Amino hexane-1,1-diphosphonic acid | N-phosphono methylene-1-amino-hexane-1,1-diphosphonic acid | 1 |
| 7 | 1-Amino dodecane-1,1-diphosphonic acid | N-phosphono methylene-1-amino dodecane-1,1-diphosphonic acid | 1 |
| 8 | 3-Amino propane-1-phosphonic acid | N,N-bis-phosphono methylene-3-amino propane-1,1-di-monophosphonic acid | 3 |
| 9 | 4-Amino pentane-1-phosphonic acid | N,N-bis-phosphono methylene-4-amino pentane-1-monophosphonic acid | 3 |
| 10 | 1,2-Diamino ethane-1,1-diphosphonic acid | Mixture of N-phosphono-methylene substituted 1,2-diamino ethane-1,1-diphosphonic acids | 2 |
| 11 | 1-Amino-3-carboxy propane-1-phosphonic acid | N-phosphono methylene-1-amino-3-carboxy propane-1-phosphonic acid | 3 |
| 12 | Propionitrile | N-phosphono methylene-1-amino propane-1,1-diphosphonic acid | 4 |
| 13 | Lauronitrile | N-phosphono methylene-1-amino dodecane-1,1-diphosphonic acid | 4 |
| 14 | Diethoxy phosphono propionitrile | N-phosphono methylene-3-phosphono-1-amino propane-1,1-diphosphonic acid | 4 |
| 15 | 1-Amino pentane-1,1-diphosphonic acid | N-phosphono methylene-1-amino pentane-1,1-diphosphonic acid | 1 |
| 16 | 1-Hydroxy-3-amino propane-1,1-diphosphonic acid | N,N-bis-phosphono methylene-3-amino-1-hydroxy-1,1-diphosphonic acid | 3 |
| 17 | 1-amino-3-hydroxy propane-1,1-diphosphonic acid | N-phosphono methylene-1-amino-3-hydroxy propane-1,1-diphosphonic acid | 1 |

-continued

| Example | Alkane reactant | Resulting amino alkane phosphonic acid | Prepared according to Example |
|---|---|---|---|
| 18 | 1-Amino-2-carboxy ethane-1,1-diphosphonic acid | N-phosphono methylene-1-amino-2-carboxy ethane-1,1-diphosphonic acid | 3 |
| 19 | 1-Amino-3-phosphono propane-1,1-diphosphonic acid | N-phosphono methylene-1-amino-3-phosphono propane-1,1-diphosphonic acid | 1 |
| 20 | 1,6-Diamino hexane-1,1,6,6-tetraphosphonic acid | N,N'-bis-phosphono methylene-1,6-diamino hexane-1,1,6,6-tetraphosphonic acid | 1 |

As stated hereinabove, the N-phosphono methylene amino alkane phosphonic acid compounds according to the present invention are useful sequestering agents forming complex compounds with bi- and polyvalent metals. They can advantageously be used, for instance, for preventing scale and deposit formation in aqueous media, as additives to cleansing solutions, for instance, for cleaning and rinsing bottles, milk cans, and the like containers, in leather tanning for cleaning, stripping, and stain removal, in textile processing, for instance, as leveling agents, in dye baths, for instance, to prevent color distortion by metal impurities, as additive to alkaline baths for treating fiber material composed of or containing native cellulose such as cotton to inhibit degradation of the cellulose chain, in peroxide bleaching baths as stabilizers, in the manufacture of paper to prevent pitch deposit, and for many other purposes in which complexing, sequestering, and/or chelating agents are used. The following examples illustrate the manner in which the phosphonic acid compounds according to the present invention can be employed without, however, limiting their usefulness to said examples.

EXAMPLE 23

Treatment of Water Used for Sterilization of Cans

Tin plate cans are placed into a 10 liter autoclave. Tap water of the following composition is used for sterilization of the cans:
Total hardness: 25° (German degrees of hardness)
Carbonate hardness: 17° (German degrees of hardness)
Chlorides: 53° mg./liter
Sulfates: 85 mg./liter
Free carbon dioxide: 40 mg./liter
Bound carbon dioxide: 125 mg./liter
pH-value: 7.2

5 cc. of N-phosphono methylene-1-amino ethane-1,1-diphosphonic acid are added to the tap water. Sterilization is effected by heating to 140° C. at about 4 atmospheres gauge. Addition of the phosphonic acid compound inhibits scale and deposit formation on the sterilized cans as well as on the walls of the autoclave.

EXAMPLE 24

250 kg. of bleached sulfite cellulose pulp known for its property of continuously causing difficulties due to resin deposition were beaten in a Hollander beater at a pulp consistency of 3% to about 78° Schopper-Riegler, i.e. so as to form a well beaten pulp suitable for producing dense sheets of the parchment-like paper. The pH-value of the slurry was 6.0.

Before starting beating, 0.5 kg. of the sodium salt of N-phosphono methylene-1-amino ethane-1,1-diphosphonic acid were added to the slurry in the Hollander beater. After beating, 0.8 kg. of the same sodium salt were admixed thereto.

When proceeding in this manner, no resinous deposits were observed on the walls of the Hollander beater, nor in the pipe lines, nor in the paper machines.

The phosphonic acids according to the present invention can be used as sequestering, complexing, and/or chelating agents for other purposes, for instance, as described in U.S. Pat. No. 3,860,391 in peroxide bleaching baths and U.S. Pat. Nos. 3,833,517 and 3,954,401 in baths for the treatment of cellulose fiber materials, and for other uses for which such agents have been used before. If desired, the alkali metal or ammonium salts or solutions thereof can also be used in place of the acids. These salts are prepared by neutralizing the phosphonic acids with the calculated amounts of alkali metal hydroxides or ammonia.

It may be mentioned that the alkali metal salts need not be prepared but that the acids as such can be added to alkaline solutions.

Of course, many changes and variations in the starting materials used, the proportions of the reactants employed, the reaction duration and conditions, the manner of working up the reaction mixtures and products, their uses and the like may be made by those skilled in the art in accordance with the aforesaid description of the invention and the claims annexed hereto.

We claim:
1. An N-phosphono methylene amino alkane phosphonic acid compound of the formula

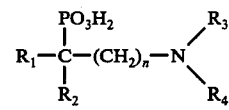

in which
$n$ is a numeral from 0 to 4;
$R_1$ indicates alkyl with 1 to 11 carbon atoms in its hydrocarbon chain,
hydroxyl,
an alkylene phosphonic acid group of the formula $-(CH_2)_n.PO_3H_2$,
the hydroxyethylene group of the formula $-C_2H_4OH$,
an alkylene carboxylic acid group of the formula $-(CH_2)_n.COOH$,
an amino alkylene group of the formula

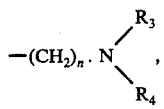

or
an 1-amino alkyl-1,1-diphosphonic acid group of the formula

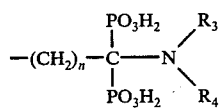

or
$R_1$ also indicates hydrogen in the case where $n$ is 1–4 and in the case where $n$ is 0 and $R_2$ is the phosphonic acid group;

$R_2$ indicates hydrogen or the phosphonic acid group;

$R_3$ indicates hydrogen or the methylene phosphonic acid group; and $R_4$ indicates the methylene phosphonic acid group.

2. The compound of claim 1, in which
$n$ is 0,
$R_1$ is hydrogen,
$R_2$ is the phosphonic acid group,
$R_3$ is hydrogen, and
$R_4$ is the methylene phosphonic acid group,
said compound being N-phosphono methylene amino methane diphosphonic acid.

3. The compound of claim 1, in which
$n$ is 0,
$R_1$ is methyl,
$R_2$ is the phosphonic acid group,
$R_3$ is hydrogen, and
$R_4$ is the methylene phosphonic acid group,
said compound being N-phosphono methylene-1-amino ethane-1,1-diphosphonic acid.

4. The compound of claim 1, in which
$n$ is 1,
$R_1$ is hydrogen,
$R_2$ is hydrogen, and
$R_3$ and $R_4$ are the methylene phosphonic acid group, said compound being N,N-bis-phosphono methylene-1-amino ethane-2-phosphonic acid.

5. The compound as defined in claim 1, wherein
$n$ is a numeral from 1 to 3
$R_1$ is hydrogen or the —$PO_3H_2$ group
$R_2$ is hydrogen or the —$PO_3H_2$ group
$R_3$ is hydrogen or the —$CH_2PO_3H_2$ group and
$R_4$ is the —$CH_2PO_3H_2$ group.

6. The compound as defined in claim 1, which is a N-phosphonic methylene-1-amino alkane-1,1-diphosphonic acid, having the formula

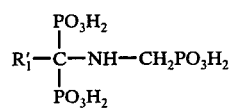

wherein
$R_1'$ indicates alkyl containing 1 to 11 carbon atoms.

7. The compound as defined in claim 1, which is a N-phosphonomethylene-1-amino-ω-carboxy-1,1-alkane-diphosphonic acid, having the formula

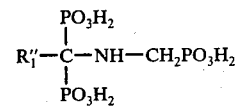

wherein
$R_1''$ indicates a —$(CH_2)_n$—COOH group wherein $n$ is 0 to 4.

8. The compound as defined in claim 1, which is a N,N-bis-phosphonomethylene-diaminoalkane-tetra phosphonic acid having the formula

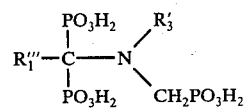

wherein
$R_1'''$ indicates a group of the formula

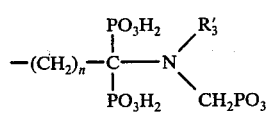

and $R_3'$ is hydrogen or a —$CH_2$—$PO_3$—$H_2$ group and $n$ is 0–4.

9. The compound as defined in claim 1, having the formula

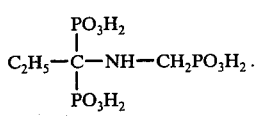

10. The compound as defined in claim 1, having the formula

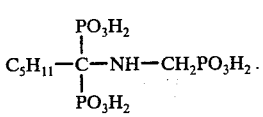

11. The compound as defined in claim 1, having the formula

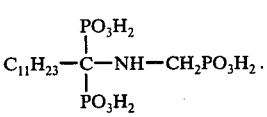

12. The compound as defined in claim 1, having the formula

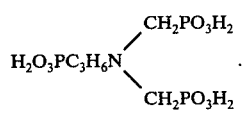

13. The compound as defined in claim 1, having the formula

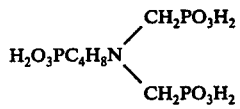

14. The compound as defined in claim 1, having the formula

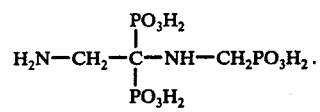

15. The compound as defined in claim 1, having the formula

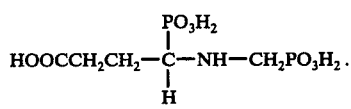

16. The compound as defined in claim 1, having the formula

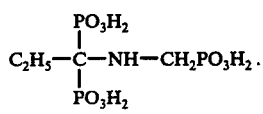

17. The compound as defined in claim 1, having the formula

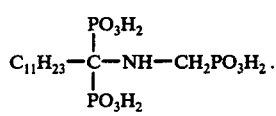

18. The compound as defined in claim 1, having the formula

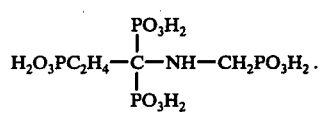

19. The compound as defined in claim 1, having the formula

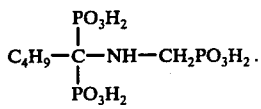

20. The compound as defined in claim 1, having the formula

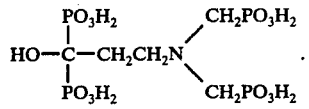

21. The compound as defined in claim 1, having the formula

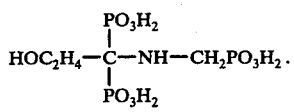

22. The compound as defined in claim 1, having the formula

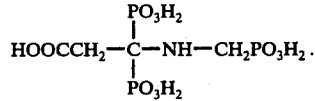

23. The compound as defined in claim 1, having the formula

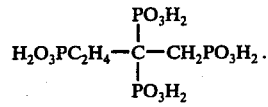

24. The compound as defined in claim 1, having the formula

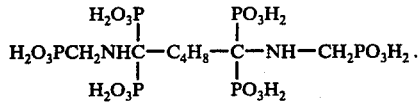

* * * * *

UNITED STATES PATENT OFFICE
CERTIFICATE OF CORRECTION

Patent No. 4,098,814          Dated  July 4, 1978

Inventor(s)  Klaus SOMMER, Guenter RAAB

It is certified that error appears in the above-identified patent and that said Letters Patent are hereby corrected as shown below:

IN THE ABSTRACT:

Lines 3 and 4, kindly delete ">N-CH-2-$PO_3H_2$" and insert instead -- >N-$CH_2$-$PO_3H_2$ --.

IN THE SPECIFICATION:

Column 6, in the Table, Example 8, kindly delete "N,N-bis-phosphono methylene-3-amino propane-1,1-dimonophosphonic acid" and insert instead -- N,N-bis-phosphono methylene-3-amino propane-1-monophosphonic acid --.

Column 6, in the Table, Example 10, kindly delete "Mixture of N-phosphono-methylene substituted 1,2-diamino ethane-1,1-diphosphonic acids" and insert instead -- Mixture of N-phosphono methylene substituted 1,2-diamino ethane-1,1-diphosphonic acids --.

Signed and Sealed this

Eighteenth Day of November 1980

[SEAL]

Attest:

SIDNEY A. DIAMOND

Attesting Officer

Commissioner of Patents and Trademarks